US010136899B2

(12) United States Patent
Jensen et al.

(10) Patent No.: US 10,136,899 B2
(45) Date of Patent: Nov. 27, 2018

(54) CLAMP FOR USE WITH A CUTTING DEVICE

(71) Applicant: PRICE INVENA APS, Copenhagen K (DK)

(72) Inventors: Knud Lykke Jensen, Kvistgård (DK); Peter Sølbeck, Vedbæk (DK)

(73) Assignee: PRICE INVENA APS, Copenhagen K (DK)

( * ) Notice: Subject to any disclaimer, the term of this patent is extended or adjusted under 35 U.S.C. 154(b) by 191 days.

(21) Appl. No.: 14/903,397

(22) PCT Filed: May 21, 2014

(86) PCT No.: PCT/EP2014/060449
§ 371 (c)(1),
(2) Date: Jan. 7, 2016

(87) PCT Pub. No.: WO2015/003845
PCT Pub. Date: Jan. 15, 2015

(65) Prior Publication Data
US 2016/0151068 A1    Jun. 2, 2016

(30) Foreign Application Priority Data

Jul. 12, 2013  (GB) .................................. 1312476.3

(51) Int. Cl.
*A61B 17/122* (2006.01)
*A61B 17/125* (2006.01)
*A61B 17/128* (2006.01)

(52) U.S. Cl.
CPC .......... *A61B 17/122* (2013.01); *A61B 17/128* (2013.01); *A61B 17/1227* (2013.01); *A61B 2017/1225* (2013.01)

(58) Field of Classification Search
CPC ................ A61B 17/122; A61B 17/083; Y10T 24/44752; Y10T 24/44761
(Continued)

(56) References Cited

U.S. PATENT DOCUMENTS 2,385,209 A * 9/1945 Joyce ........................ F16L 3/24
                                                            24/339
3,429,985 A * 2/1969 Czigler ..................... F16L 3/12
                                                            174/164

(Continued)

FOREIGN PATENT DOCUMENTS

CN      1469725 A1    1/2004
CN      2650714 Y    10/2004
(Continued)

OTHER PUBLICATIONS

International Search Report for PCT/EP2014/060449, ISA/EP, Rijswijk, NL, dated Jul. 28, 2014.

*Primary Examiner* — Kathleen Holwerda
(74) *Attorney, Agent, or Firm* — Harness, Dickey & Pierce, P.L.C.

(57) ABSTRACT

A clamp for use in a clamping and cutting device comprising a first leg (10), second leg (14) and third leg (22) which together form a cavity capable of receiving an object to be clamped when open, wherein the second leg (14) has a recessed section (20) such that the third leg (22) fits into the recessed section (20) when the clamp is closed, and a clamping and cutting device for clamping and cutting an object.

18 Claims, 6 Drawing Sheets

(58) Field of Classification Search
USPC .......... 606/120, 151, 157, 158; 24/543;
248/316.5
See application file for complete search history.

(56) References Cited

U.S. PATENT DOCUMENTS

| | | | |
|---|---|---|---|
| 3,766,925 A | 10/1973 | Rubricius | |
| 3,995,795 A * | 12/1976 | Hogan | F16L 3/1233 |
| | | | 248/68.1 |
| 4,596,351 A | 6/1986 | Fedotov et al. | |
| 5,285,556 A | 2/1994 | Shorin et al. | |
| 5,622,341 A * | 4/1997 | Stana | F16L 3/13 |
| | | | 248/221.11 |
| 5,697,938 A | 12/1997 | Jensen et al. | |
| 5,937,488 A * | 8/1999 | Geiger | F16L 3/1033 |
| | | | 24/16 PB |
| 5,947,980 A | 9/1999 | Jensen et al. | |
| 6,421,920 B1 * | 7/2002 | Jensen | A61B 17/122 |
| | | | 30/124 |
| 6,935,599 B2 * | 8/2005 | van Walraven | F16L 3/12 |
| | | | 24/16 PB |
| 7,178,203 B2 * | 2/2007 | Pearson | F16L 3/137 |
| | | | 24/16 PB |
| 7,329,266 B2 | 2/2008 | Royse et al. | |
| 2004/0193189 A1 | 9/2004 | Kortenbach et al. | |
| 2006/0129170 A1 | 6/2006 | Royse et al. | |

FOREIGN PATENT DOCUMENTS

| | | |
|---|---|---|
| EP | 1462061 A2 | 9/2004 |
| GB | 2078849 A | 1/1982 |
| WO | 1985004091 A1 | 9/1985 |
| WO | WO-95/08953 A1 | 4/1995 |
| WO | WO-98/44851 A1 | 10/1998 |
| WO | WO-03/011150 A1 | 2/2003 |

* cited by examiner

CLAMP FOR USE WITH A CUTTING DEVICE

CROSS-REFERENCE TO RELATED APPLICATIONS

This application is a 371 U.S. National Stage of International Application No. PCT/EP2014/060449, filed May 21, 2014, which claims the benefit of and priority to United Kingdom Application No. GB 1312476.3, filed Jul. 12, 2013. The entire disclosures of the above applications are incorporated herein by reference.

The present invention relates to an improved clamp for use in devices for clamping and cutting objects, e.g. for clamping and cutting an umbilical cord.

WO95/08953 discloses a device for squeezing and cutting members such as an umbilical cord that possesses substantial advantages in ease of use, safety and ease of construction over previous devices. Said device comprised a first clamp, a second clamp and a clamp holder which when assembled correctly would allow the clamping and cutting of an umbilical cord.

WO98/44851 discloses an improvement upon the device described in WO95/08953 wherein the design of the clamps were improved and the improved design of the clamp holder allowed a first clamp to be disengaged from the clamp holder in a much more rapid and reliable fashion.

SUMMARY OF THE INVENTION

The herein presented invention further improves upon the design of a clamp for use, for example, in a device as disclosed in WO95/08953 and/or in WO98/44851. The open clamp configuration of the assembled device as disclosed in WO95/08953 and WO98/44851 proved to be problematic as the item to be cut (preferably an umbilical cord) was prone to misaligning with or disengaging from the apparatus prior to cutting. The herein described improved clamp introduces a third leg to the clamp which effectively secures the object to be cut (umbilical cord) in the apparatus and thus stops it from misaligning or disengaging prior to cutting. This modification improves the ease of use of the device.

In a first aspect, the present invention relates to a clamp for use in a clamping and cutting device, said clamp comprising:

a first leg (10) having an inner face comprising a clamping bed (12), a second leg (14) attached at one end to the first leg (10) at one end of said clamping bed (12) by a resilient hinge (16) by which the legs are sprung apart, said second leg having an inner face comprising a clamping bed (18) extending part of the length of the inner face of said second leg from the hinge attached end of said second leg, and a recessed section (20) extending from the clamping bed (18) of said second leg to an opposite end of said second leg;

a third leg (22) attached to said first leg (10) at an opposite end of said clamping bed (12) of the first leg (10) by a resilient hinge (24) by which the legs are sprung apart, said third leg comprising a clamping bed (26) extending the length of an inner face of said third leg, and a contact section (28) on an outer face of said third leg;

wherein said first leg (10), said second leg (14) and said third leg (22) together form a cavity capable of receiving an object to be clamped, wherein pressing said second leg (14) towards the first leg (10) against the resilience of the hinge (16) joining them causes said recessed section (20) of the second leg to contact said contact section (28) on said third leg (22) such that said third leg is pressed towards the first leg against the resilience of the hinge (24) joining them, wherein said recessed section (20) is recessed such that said third leg (22) fits into said recessed section 20 when said clamp is closed, and wherein the clamping beds (18, 26) of said second and third legs (14, 22) together form a contiguous clamping bed for clamping a received object against the clamping bed of the first leg when said clamp is closed.

Preferably, the clamping bed (12) of the first leg and/or the clamping beds (18, 26) of the second and third legs may comprise a row of teeth. Preferably still, within the hinge (16) may be a flexible guard (30) for preventing the object to be clamped in use passing into the hinge and escaping from the clamping beds (12, 18, 26) of the clamp.

In a preferred embodiment of the invention said first leg (10) may be extended beyond said third leg (22) to form an elongate section (32). Preferably, said elongate section (32) may be capped by a pusher section (34), wherein said pusher section (32) may further comprise a thumb engaging surface (36) formed on an enlarged head portion (38). Furthermore, said elongate section (32) may comprise an abutment surface (52) facing in the direction of said second leg (14).

In another preferred embodiment of the invention said clamp may comprise a T-shaped rail (40) incorporating a flange (42) attached to the outer face of said first leg (10).

Preferably, said flange (42) may be extended spaced from the hinge (16) said second leg (14) to form a resilient tail (44), wherein said tail may comprise a tooth (46) on an outer face of said flange, said tooth comprising an abutment surface facing in the direction of the third leg.

In another preferred embodiment of the invention said clamp may comprise a rail (48) attached to the outer face of the second leg (14).

In another preferred embodiment of the invention said clamp may comprise a catch mechanism for latching said first leg (10) to said second leg (14) when the clamp is closed.

The herein described clamp may be moulded from a plastics material, such as, but not limited to, nylon.

In another aspect, the present invention relates to a clamping and cutting device comprising:

a first clamp (88), wherein said first clamp comprises a first leg (90) joined to a second leg (92) by a hinge (94) at one end thereof and openable apart to receive an object to be cut, a second clamp, wherein said second clamp is a clamp as claimed in any preceding claim, a clamp holder (56) comprising cutting means (66) and means (80, 82, 84, 86) for supporting said first and second clamps side by side with one another with said cutting means (66) between them and for guiding said clamps in a sliding movement within said clamp holder to advance said cutting means between said clamps to cut a said object in use whilst compressing the legs of said clamps to clamp said object, and pusher means (34) for sliding said clamps through said clamp holder.

In a preferred embodiment, said means (82, 86) for supporting said first clamp (88) may disengage from said clamp when said clamp is slid to a predetermined release point with respect to said clamp holder, preferably such that the clamp may be removed from said clamp holder in two directions each orthogonal to the direction of said sliding movement.

In a preferred embodiment, said first clamp may be a clamp of the invention as described herein.

In a preferred embodiment, an abutment (46, 85) may be provided obstructing removal of said second clamp by sliding movement thereof out of said clamp holder.

Preferably, the object to be clamped and/or cut by the clamp and/or clamping and cutting device as described herein is an umbilical cord.

FIGURES

Figure 3:
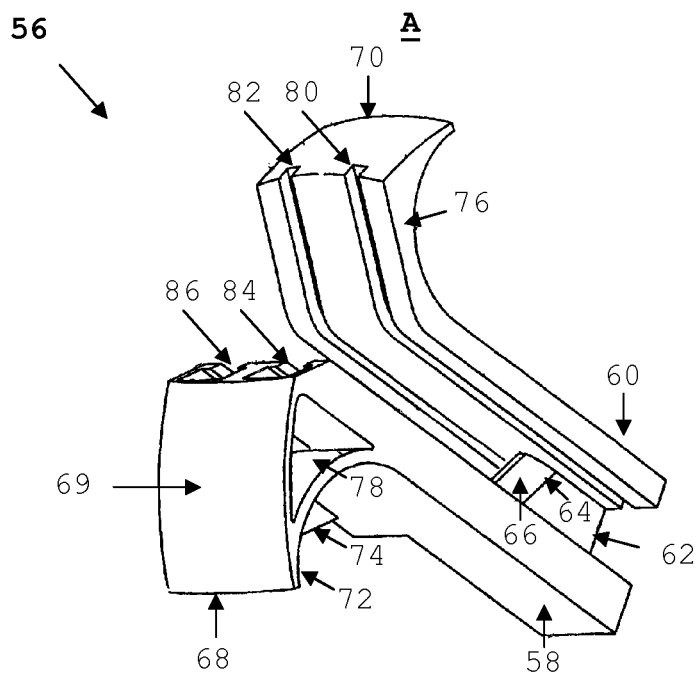
Figure 3:
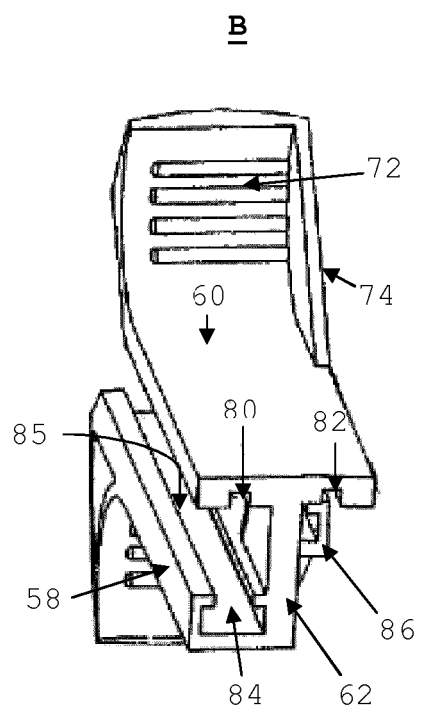

FIG. 3, view A and view B show respectively a perspective view from one end and a perspective view from an opposite end of a preferred embodiment of a clamp holder.

Figure 4:
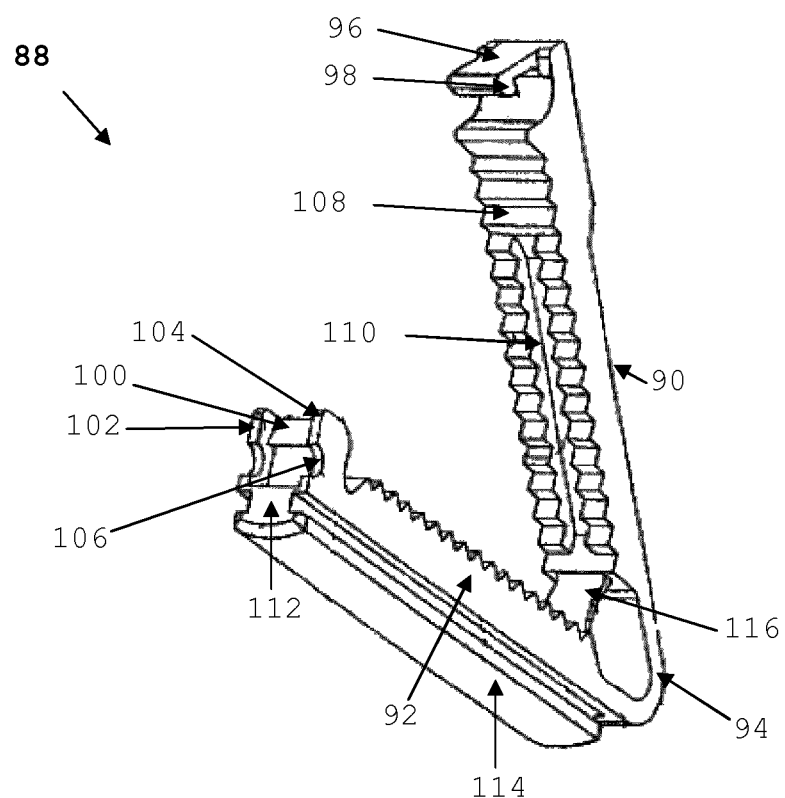

FIG. 4 shows a perspective view from below of a preferred embodiment of a first clamp (baby side) for use in a preferred embodiment of a cutting and clamping device of the invention.

Figure 5:
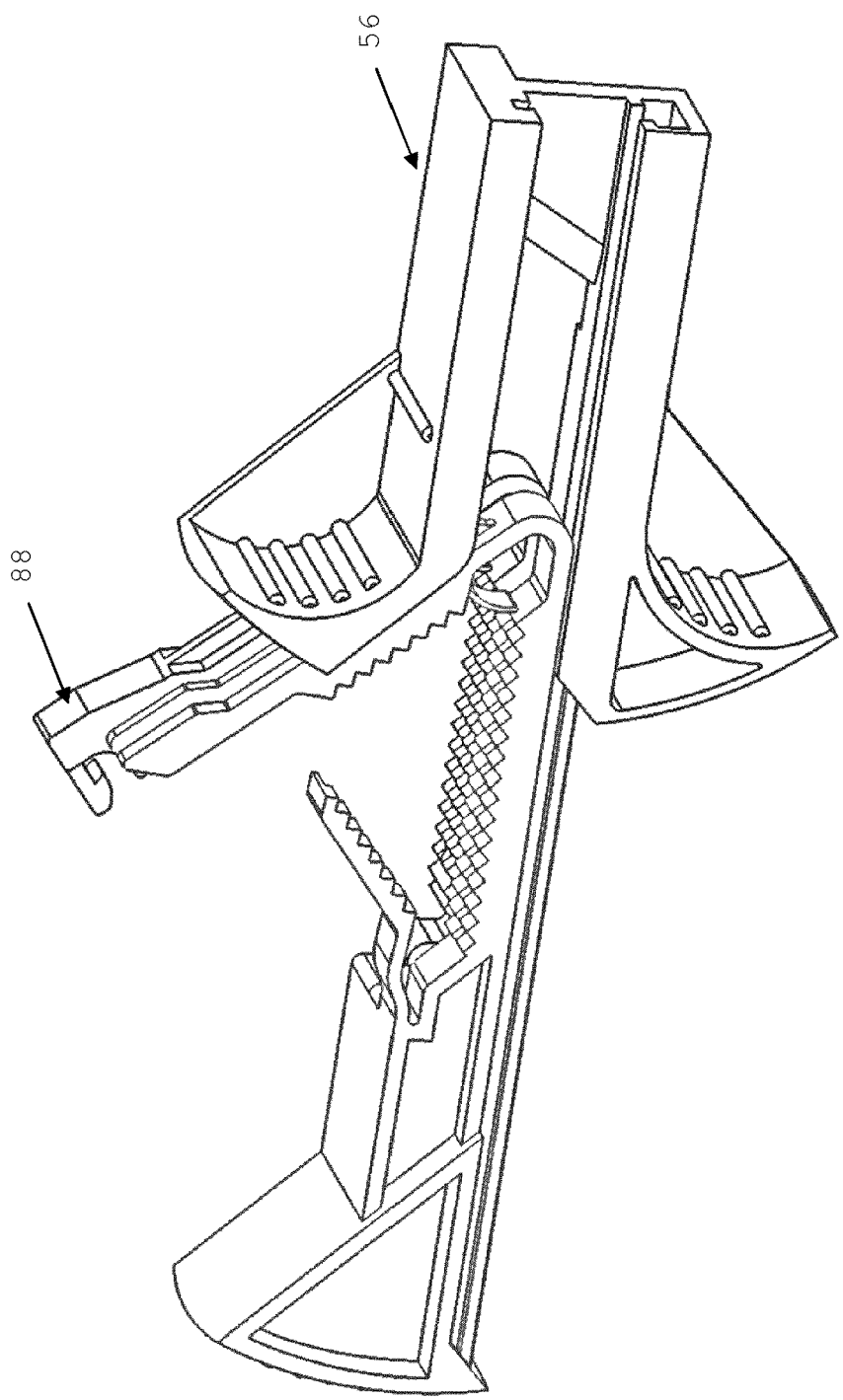

FIG. 5 shows a perspective view from above and from one side of a preferred embodiment of an assembled clamping and cutting device of the invention.

Figure 6:
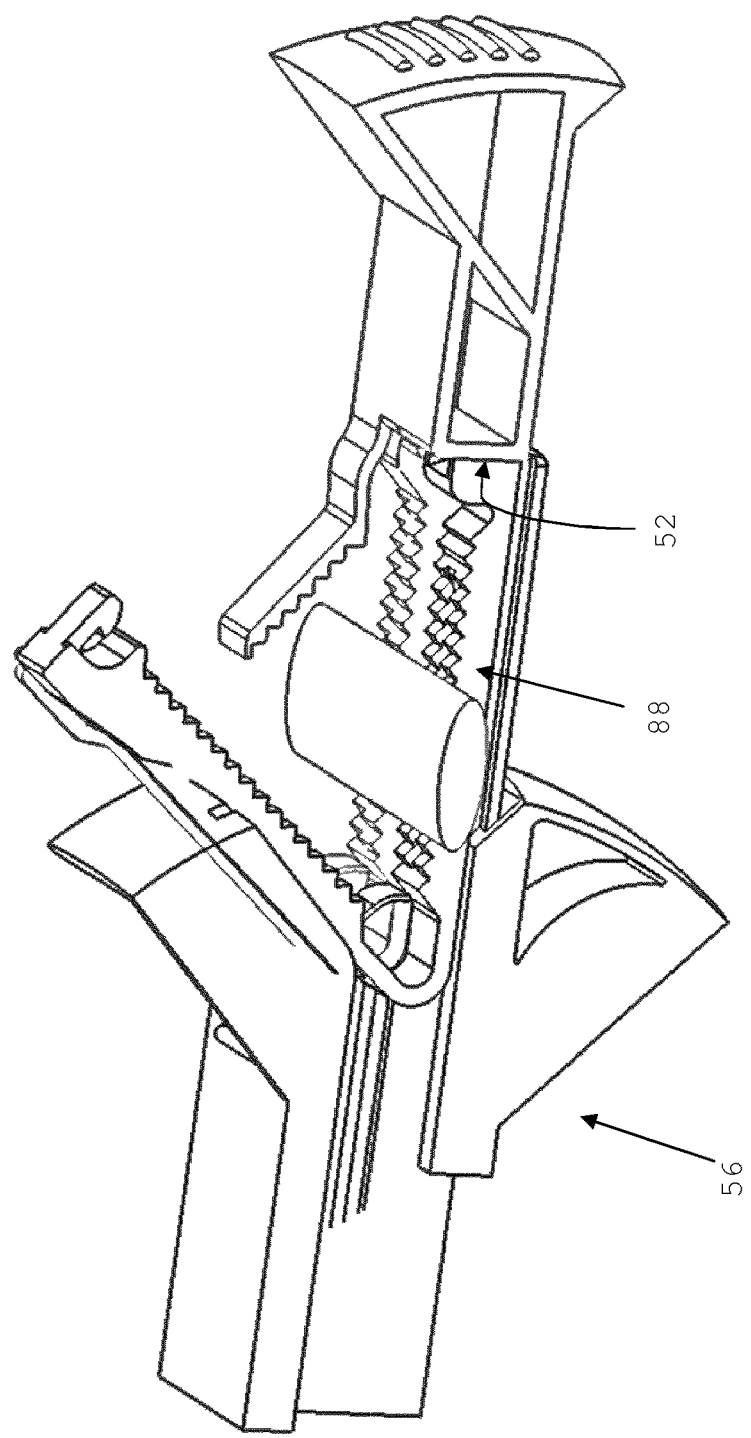

FIG. 6 shows a perspective view from above and from an opposite side of the assembled device of FIG. 5 showing the configuration of the device when an object (umbilical cord) to be cut is engaged in the apparatus.

DESCRIPTION OF PREFERRED EMBODIMENTS OF THE INVENTION

Figure 1:
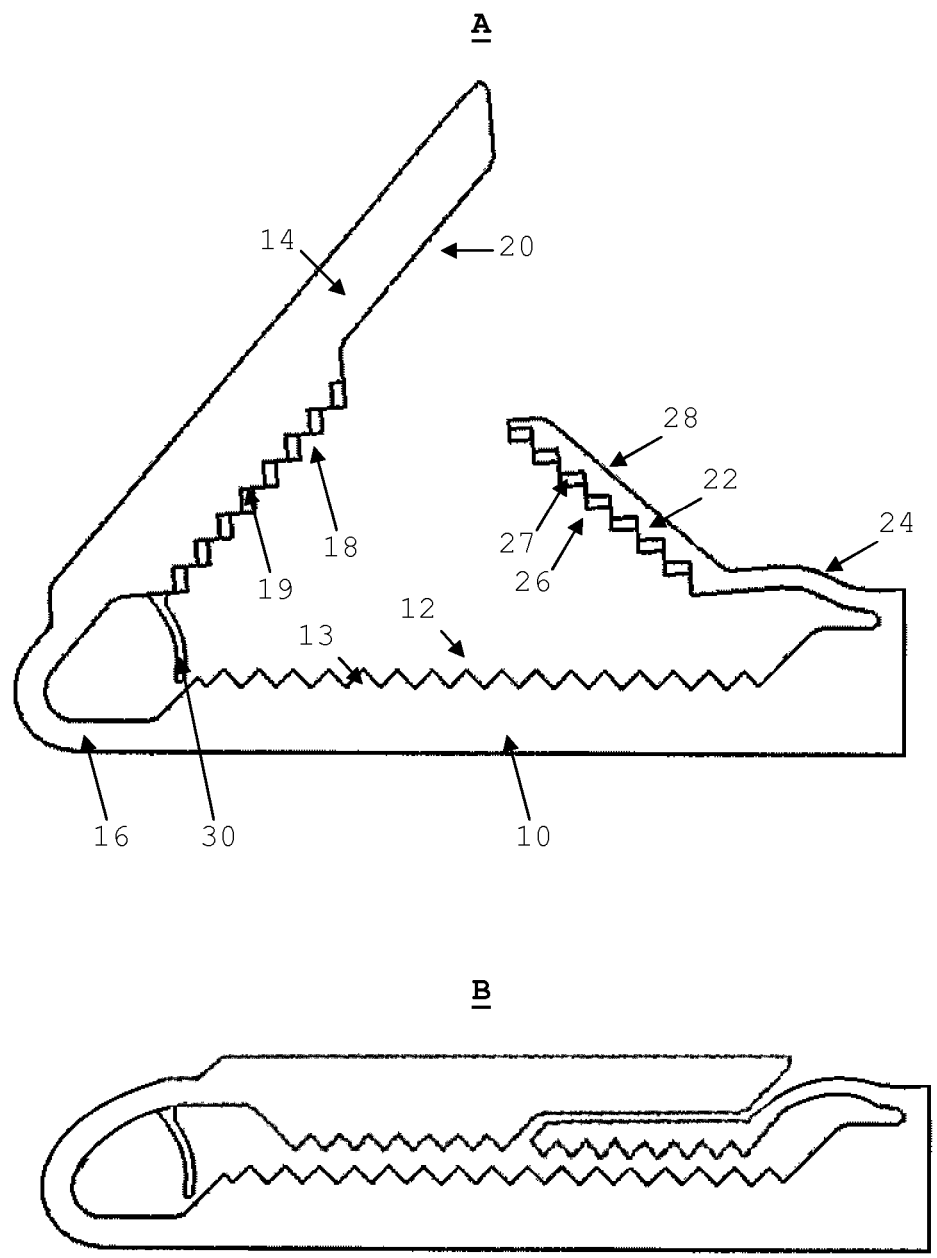
FIG. 1 shows in side view a first general embodiment of a clamp of the present invention; view A shows the open configuration and view B shows the closed configuration.

FIG. 1 shows a first general embodiment of a clamp of the present invention. The clamp comprises a first leg 10 having an inner face comprising a clamping bed 12. To one end of the first leg is attached a second leg 14 by a resilient hinge 16 by which the legs are sprung apart. The second leg has an inner face comprising a clamping bed 18 extending part of the length of the inner face of said second leg from the hinge attached end of said second leg, and a recessed section 20 extending from the clamping bed 18 of said second leg to an opposite end of said second leg. Attached to the opposite side of the clamping bed 12 of the first leg 10 is a third leg 22. The third leg 22 is attached to said first leg 10 by a resilient hinge 24 by which the legs are sprung apart. The third leg 22 comprises a clamping bed 26 extending the length of the inner face of said third leg, and a contact section 28 on the outer face of said third leg.

The clamping bed 12 of the first leg and the clamping beds 18, 26 of the second and third legs may comprise respective rows of teeth 13, 19, 27. Within the hinge 16 there is a flexible guard 30 for preventing the object to be clamped in use passing into the hinge and escaping from the clamping beds 12, 18, 26 of the clamp.

The first leg 10, second leg 14 and third leg 22 together form a triangular shaped cavity capable of receiving an object to be clamped.

Pressing the second leg 14 towards the first leg 10 against the resilience of the hinge 16 joining them causes the recessed section 20 of the second leg to contact the contact section 28 on the outer face of the third leg 22, which in turn causes the third leg to be pressed towards the first leg 10 against the resilience of the hinge 24 joining them.

FIG. 1 B shows the clamp when it is closed. The recessed section 20 of the second leg 14 is recessed such that the third leg 22 fits into the recessed section 20. The clamping beds 18, 26 of the second and third legs 14, 22 together form a contiguous clamping bed for clamping a received object against the clamping bed of the first leg when said clamp is closed.

Figure 2:
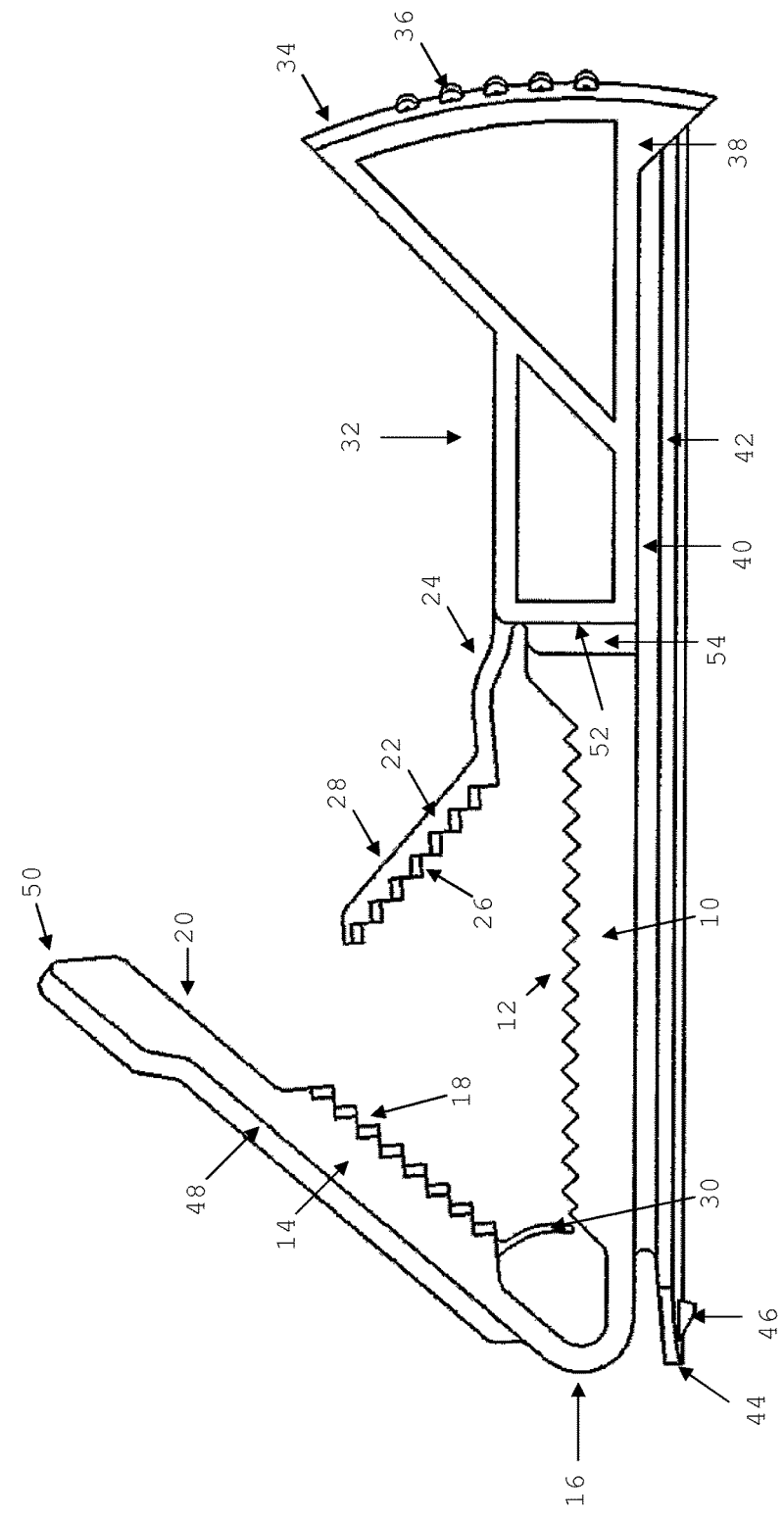
FIG. 2 shows a side view of a preferred embodiment of a mother's side umbilical cord clamp of the present invention.

FIG. 2 shows a side view of a preferred embodiment of a mother's side umbilical cord clamp of the present invention. The first leg 10 is extended beyond said third leg 22 to form an elongate section 32. The elongate section 32 is capped by a pusher section 34, and said pusher section 32 comprises a thumb engaging surface 36 formed on an enlarged head portion 38. Furthermore, said elongate section 32 comprises an abutment surface 52 facing in the direction of said second leg 14.

The clamp further comprises a T-shaped rail 40 incorporating a flange 42 attached to the outer face of the first leg 10. Said flange 42 is extended spaced from the hinge 16 said second leg 14 to form a resilient tail 44. The tail comprises a tooth 46 on an outer face of the flange, said tooth comprising an abutment surface facing in the direction of the third leg.

Additionally a rail 48 is attached to the outer face of the second leg.

In an optional variant (not shown) the clamp of the invention may comprise a catch mechanism for latching said first leg 10 to said second leg 14 when the clamp is closed generally as shown in the known clamp of FIG. 4. Adding such a catch mechanism would allow a clamp of the current invention to be used for clamping an umbilical cord on the baby's side and not restrict such a clamp to use on the mother's side only.

The herein described clamps may be moulded from a plastics material, such as, but not limited to, nylon.

Preferred Embodiment of a Clamp of the Invention in a Clamping and Cutting Device A clamp of the invention as shown in FIG. 1 or 2 may be combined with a clamp holder such as that shown in FIG. 3 and a 'first clamp' such as that shown in FIG. 4 to produce a cutting and clamping device as shown in FIGS. 5 and 6.

The clamp of the present invention may however be used in any suitable device and its use is not limited to the hereinafter disclosed embodiment.

FIG. 3 shows a known example of a clamp holder which may be used in a clamping and cutting device of the invention. The clamp holder 56 comprises a first wall member 58 and a second wall member 60. In a rear portion of the holder, the wall members 58 and 60 extend in parallel spaced relationship and are connected by a web 62 which extends forward from the rear end of the device along approximately half the length of the parallel portions of the wall members 58 and 60. At its forward end, the web 62 slopes from the wall member 58 rearwardly to its connection to the wall member 60 as a forward edge 64. Within the thickness of the web there is set a metal knife blade 66 whose cutting edge slopes parallel to the forward edge 64 of the web.

From just forward of the most forward point of the knife blade 66 back to the rear of the clamp holder 56, the wall member 58 has a cut away portion such that all of the wall member to one side of the web is omitted. Optionally, the wall member 60 may be similarly cut away in the region opposite to the cut away in the wall member 58.

At the forward ends of the wall members 58 and 60, there are provided a pair of finger engagement wings 68, 70 integrally moulded with the wall members 58, 60 and extending laterally out therefrom. These include a concave finger engaging surface 72 defining a finger receiving passageway extending from the upper surface of the clamp holder downwards to an end plate 74 in each case. The end plate 74 serves to close the finger receiving passageway defined by the surface 72 on each wing. Wall member 60 has an outwardly diverging portion 76 at its forward end whilst wall member 58 extends in a straight line to the front of the device. The front of wing 68 is formed as a convex surface 69 and the space between the convex surface 69 and concave face 72 embraces an approximately triangular cross-section hollow 78 to save material and to second shrinkage.

Above and below the web 62, the wall members 58, 60 together with the web 62 define a pair of channels. Each channel is for receiving a respective clamp of the invention as described hereafter. To guide movement of the clamps, each channel is provided with guide slots. In wall member 60, there are provided guide slots 80 and 82, each of which is a plain rectangular slot extending from the rear end of wall member 60 to its front end, including the outwardly diverging or flaring portions 76.

In wall member 58, each slot 84, 86 is undercut in a T-shape. The surface of wall member 58 forming the top of the head of the "T" of the slot 84 has a dog 85 providing a rear facing abutment surface.

A first clamp of a known type which may be used with the device is shown in FIG. 4. This clamp may be used to clamp an umbilical cord on the baby's side. The clamp 88 comprises a pair of legs 90, 92 joined at a resilient integrally moulded hinge 94 by which the legs are sprung apart. At their free ends, the legs are provided with a catch mechanism comprising a catch 96 extending inwardly from leg 90 and having a hooked end 98 which co-operates with an outwardly facing abutment surface on a dog 100 provided at the free end of leg 92. Dog 100 is provided at the base of a channel extending across the end of leg 92 and defined by forwardly protruding channel walls 102, 104 in each of which is provided a forwardly facing arcuate depression 106.

The interior surface of each leg 90, 92 may be provided with a row of transversely extending teeth 108 for gripping a cord when the clamp is shut. Running longitudinally of each leg central within the width of the teeth 108 may be an open slot 110 which assists in preventing movement of the clamp along the length of the cord in use.

Leg 92 is provided on its exterior surface with a rail 112 bearing a flange 114 producing a T-shape, matching slot 86 of the clamp holder in which it may be adapted to be received.

On the exterior of the other leg (not shown) there is provided a rail to engage in slot 34 of the clamp holder.

Finally, the clamp 88 has extending from leg 92 a flexible guard 116 for preventing the cord in use passing into the hinge 94 and escaping from the teeth of the clamp.

Optionally, a first clamp which may be used with the device may be a clamp of the invention as described herein.

The preferred embodiment of the clamp of the invention as shown in FIG. 2 and described supra may be provided as a second clamp for the device. This clamp is intended to clamp an umbilical cord on the mother's side.

The T-shaped rail 40 incorporating flange 42 is similar to that on the first clamp and adapted to be received in T-shaped slot 84 of the clamp holder. The resilient tail 44 bearing a tooth 46 having a forwardly facing (with respect to the clamp holder) abutment surface is adapted to engage behind the rearward facing abutment surface of the dog 85 of the slot 84.

Rail 48 attached to leg 14 runs in slot 80 of the clamp holder.

Adjacent the end of leg 10, the extended section 32 has a rearward facing (with respect to the clamp holder) abutment surface 52 with a rearward facing protrusion 54.

For use, the device is assembled by passing the rearward end of the T-shaped rail 40 into the forward end of the T-shaped slot 84 of the clamp holder until the tooth 46 passes the dog 85, thus retaining the clamp in the clamp holder.

The clamp 88 is assembled into the clamp holder by passing the tail end of the T-shaped rail 112 into the mouth of the slot 86 of the clamp holder. The device is then ready for use.

When the apparatus is fully assembled both clamps are open as shown in FIG. 5. The device may be packaged in this form and may be supplied ready for use from the factory in which it is made.

In use to cut an umbilical cord, the operator grips the device by placing the operators thumb against the pushing means 36 and placing the first and second fingers into the finger receiving passageways defined by the arcuate surfaces 72 until they abut against the plates 74 of the clamp holder. The smooth underside of the clamp holder is then placed against the surface of the stomach of a baby during delivery. The umbilical cord is passed into the open mouths of the clamps by depressing the third leg 22. Once the umbilical cord has traversed the third leg 22 and is in mouths of the clamps, the third leg is automatically returned to its original position by the hinge 24. As is shown in FIG. 6, when the third leg is returned to its original position the umbilical cord becomes trapped within a triangular cavity formed by legs 10, 14 and 22, which ensures that said cord remains within the clamps during operation of the device.

By then pressing the pusher head 38 at the head of the preferred embodiment of the clamp of the invention with the thumb as if operating a syringe, the clamps are driven to slide synchronously through the clamp holder.

The pushing action is conveyed to the clamp 88 by the engagement of the rearward facing abutment surface 52. As the clamp 88 comes into the parallel walled portion of its channel in the clamp holder, the catch 96 is driven between the projecting walls 102, 104 to become closed and engaged. When the head end of the clamp 88 reaches the rear end of its T-shaped slot 86 the clamp 88 is ejected from its channel in the clamp holder and is free to move away from the wall member 60. As the clamp of the present invention comes into the parallel walled portion of its channel in the clamp holder, the leg 14 is driven downward such that the recessed surface 20 contacts the contact surface 28 of the third leg 22 which drives the clamping element 26 downward to contact the clamping bed 10. When the clamp is fully engaged in the clamp holder 56 the clamping elements 18, 26 together form a contiguous clamping element.

The clamp 88 may be made from a different coloured material from the rest of the device. Suitably, all of the components except the cutting blade may be moulded in plastics such as nylon.

Many modifications and variations of the invention as described with reference to the specific embodiment may be made within the scope of the invention. For instance, instead of one clamp remaining captive in the clamp holder, both clamps may be made to eject from the clamp holder in a similar way on being pushed fully home. The pusher may be provided with its guide slot in the clamp holder and may push against each clamp in the same way that it pushes against clamp 42 in the illustrated embodiment.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A clamp comprising:
   a first leg having an inner face comprising a clamping bed,
   a second leg attached at one end to the first leg at one end of said clamping bed by a resilient hinge by which the legs are sprung apart, said second leg having an inner face comprising a clamping bed extending part of the length of the inner face of said second leg from the hinge attached end of said second leg, and a recessed section extending from the clamping bed of said second leg to an opposite end of said second leg;
   a third leg attached to said first leg at an opposite end of said clamping bed of the first leg by a resilient hinge by which the third and first legs are sprung apart, said third leg comprising a clamping bed extending the length of an inner face of said third leg, and a contact section on an outer face of said third leg;
   wherein said first leg, said second leg and said third leg together form a cavity capable of receiving an object to be clamped,
   wherein pressing said second leg towards the first leg against the resilience of the hinge joining them causes said recessed section of the second leg to contact said contact section on said third leg such that said third leg is pressed towards the first leg against the resilience of the hinge joining them,
   wherein said recessed section is recessed such that said third leg fits into said recessed section when said clamp is closed,
   wherein the clamping beds of said second and third legs together form a contiguous clamping bed for clamping a received object against the clamping bed of the first leg when said clamp is closed, and
   wherein said first leg is parallel to said second and third legs when said clamp is closed.

2. The clamp as claimed in claim 1, wherein said first leg is extended beyond said third leg to form an elongate section.

3. The clamp as claimed in claim 2, wherein said elongate section is capped by a pusher section.

4. The clamp as claimed in claim 3, wherein said pusher section comprises a thumb engaging surface formed on an enlarged head portion.

5. The clamp as claimed in claim 2, wherein said elongate section comprises an abutment surface facing in the direction of said second leg.

6. The clamp as claimed in claim 1, wherein said clamp comprises a T-shaped rail incorporating a flange attached to an outer face of said first leg.

7. The clamp as claimed in claim 6, wherein said flange is spaced from the hinge of said second leg to form a resilient tail, wherein said tail comprises a tooth on an outer face of said flange, said tooth comprising an abutment surface facing in the direction of the third leg.

8. The clamp as claimed in claim 1, wherein said clamp comprises a rail attached to an outer face of the second leg.

9. The clamp as claimed in claim 1, wherein said clamp further comprises a catch mechanism for latching said first leg to said second leg when the clamp is closed.

10. The clamp as claimed in claim 1, wherein said clamp is molded from a plastics material.

11. The clamp as claimed in claim 1, wherein said cavity formed from said first leg, said second leg and said third leg is triangular-shaped.

12. The clamp as claimed in claim 1, wherein said clamping bed of the first leg and/or the clamping beds of the second and third legs comprise a row of teeth.

13. A clamping and cutting device comprising:
    a first clamp,
    a second clamp including:
    a first leg having an inner face comprising a clamping bed,
       a second leg attached at one end to the first leg at one end or said clamping bed by a resilient hinge by which the legs are sprung apart, said second leg having an inner face comprising a clamping bed extending part of the length of the inner face of said second leg from the hinge attached end of said second leg, and a recessed section extending from the clamping bed of said second leg to an opposite end of said second leg;
    a third leg attached to said first leg at an opposite end of said clamping bed of the first leg by a resilient hinge by which the third and first legs are sprung apart, said third leg comprising a clamping bed extending the length of an inner face or said third leg, and a contact section on an outer face of said third leg;
    wherein said first leg, said second leg and said third leg together form a cavity capable of receiving an object to be clamped,
    wherein pressing said second leg towards the first leg against the resilience of the hinge joining them causes said recessed section of the second leg to contact said contact section on said third leg such that said third leg is pressed towards the first leg against the resilience of the hinge joining them,
    wherein said recessed section is recessed such that said third leg fits into said recessed section when said clamp is closed,
    wherein the clamping beds of said second and third legs together form a contiguous clamping bed for clamping a received object against the clamping bed of the first lea when said clamp is closed, and
    wherein said first leg is parallel to said second and third legs when said clamp is closed,
    wherein said first clamp comprises a first leg joined to a second leg by hinge at one end thereof and openable apart to receive an object to be cut,
    a clamp holder comprising a blade and a plurality of slots that receive and support said first and second clamps side by side with said blade between them, said plurality of slots guiding said first and second clamps in a sliding movement within said clamp holder to advance said blade between said first and second clamps to cut said object in use whilst compressing the legs of said first and second clamps to clamp said object,
    and a thumb engaging surface for sliding said clamps through said clamp holder.

14. The clamping and cutting device as claimed in claim 13, wherein said plurality of slots disengage from said first clamp when said first clamp is slid to a predetermined release point with respect to said clamp holder.

15. The clamping and cutting device as claimed in claim 14, wherein the first clamp can be removed from said clamp holder in two directions each orthogonal to the direction of said sliding movement.

16. The clamping and cutting device as claimed in claim 13, wherein said first clamp is a clamp as claimed in claim 1.

17. The clamping and cutting device as claimed in claim 13, wherein said first clamp is a clamp as claimed in claim 9.

18. The clamping and cutting device as claimed in claim 13, wherein an abutment is provided obstructing removal of said first clamp by sliding movement thereof out of said clamp holder.

* * * * *